(12) United States Patent
Inoue et al.

(10) Patent No.: US 8,248,596 B2
(45) Date of Patent: Aug. 21, 2012

(54) CRYOSTAT

(75) Inventors: Yoshihisa Inoue, Toyonaka (JP); Kido Okamoto, Katano (JP); Takehiko Wada, Sendai (JP); Tatsuo Nakagawa, Daito (JP)

(73) Assignee: Japan Science and Technology Agency, Kawaguchi-shi, Saitama (JP)

( * ) Notice: Subject to any disclaimer, the term of this patent is extended or adjusted under 35 U.S.C. 154(b) by 0 days.

(21) Appl. No.: 13/062,276

(22) PCT Filed: Sep. 2, 2009

(86) PCT No.: PCT/JP2009/065359
§ 371 (c)(1),
(2), (4) Date: Mar. 4, 2011

(87) PCT Pub. No.: WO2010/026997
PCT Pub. Date: Mar. 11, 2010

(65) Prior Publication Data
US 2011/0170093 A1  Jul. 14, 2011

(30) Foreign Application Priority Data

Sep. 4, 2008  (JP) .................................. 2008-227631

(51) Int. Cl.
*G01N 21/01* (2006.01)
(52) U.S. Cl. ....................................... 356/244; 356/246
(58) Field of Classification Search .................. 356/244, 356/246, 236, 250
See application file for complete search history.

(56) References Cited

U.S. PATENT DOCUMENTS
4,995,727 A  2/1991 Kawagoe et al.

FOREIGN PATENT DOCUMENTS

| JP | 63-305221 A | 12/1988 |
|----|-------------|---------|
| JP | 6-053961 A | 7/1994 |
| JP | 8-166331 A | 6/1996 |
| JP | 11-023431 A | 1/1999 |
| JP | 2002-071551 A | 3/2002 |
| JP | 2002-310907 A | 10/2002 |

OTHER PUBLICATIONS

Guidebook for Instrumental Analysis, edited by The Japan Society for Analytical Chemistry, pp. 275.
International Search Report of PCT/JP2009/065359, date of mailing Oct. 6, 2009.

*Primary Examiner* — Tri T Ton
(74) *Attorney, Agent, or Firm* — Westerman, Hattori, Daniels & Adrian, LLP

(57) ABSTRACT

A cryostat includes: a casing having an inlet port and exit port; a cell housing provided in the casing; a temperature controller for adjusting the temperature of the cell; a first optical path tube for guiding a light beam from the inlet port of the casing to the cell housing; a second optical path tube for guiding the light beam having passed through the cell housing to the exit port of the casing; first and second optical windows disposed at openings, exposed to the outside, of the first and second optical path tubes, respectively; and sealing materials having a water vapor transmission rate of 30000 cc·cm$^2$·mm·sec·cm Hg×10$^{10}$ or lower, disposed at the peripheries of the first and second optical windows to seal the first and second optical path tubes.

8 Claims, 17 Drawing Sheets

FLUORESCENCE
LIGHT

CRYOSTAT

TECHNICAL FIELD

The present invention relates to a cryostat.

BACKGROUND ART

Optical measuring devices such as circular dichroism spectrometers, ultraviolet-visible spectrophotometers, and spectrofluorimeters are sometimes provided with cryostats for accommodating a cell. A cell accommodated in a cryostat is irradiated with a light beam to measure a spectrum, thereby allowing the chirality, structure, and the like of a compound to be determined (Non-patent Literature 1).

When an optical measurement is performed for a long period of time, there is a problem such that water vapor flows into the cryostat; consequently, water condenses on the surface of the cell, and the optical measurement cannot be performed effectively. In order to solve such a problem, operations for evacuating the cryostat and like operations have been conventionally performed.

However, in order to evacuate the cryostat, a special mechanism for maintaining vacuum or the like must be placed thereinside. Therefore, the internal structure becomes complicated, which is a cause of an increase in the size of cryostats.

Accordingly, the development of a cryostat that is small-sized and capable of effectively preventing water condensation on the surface of the cell has been strongly desired.

In addition, when the inside of the cryostat is under vacuum, optical windows may be distorted, and therefore the CD spectra cannot be accurately measured in some cases. Accordingly, the development of a cryostat with little distortion in optical windows even when the inside of the cryostat is under vacuum has been desired.

CITATION LIST

Non-Patent Literature

NPL 1: Guidebook for instrumental analysis, edited by The Japan Society for Analytical Chemistry

SUMMARY OF INVENTION

Technical Problem

A primary object of the present invention is to provide a cryostat that is small-sized and capable of effectively preventing water condensation on the surface of the cell.

Solution to Problem

The inventors of the present invention have conducted extensive research. As a result, they found that the above object can be achieved by using a specific sealing material to seal the optical windows inside the cryostat, and accomplished the present invention.

That is, the present invention relates to the following cryostat:

1. A cryostat comprising:
a casing in which an inlet port and an exit port are formed;
a cell housing provided in the casing;
a temperature control means for adjusting the temperature of the cell;
a first optical path tube for guiding a light beam entering the inlet port of the casing to the cell housing;
a second optical path tube for guiding the light beam that has passed through the cell housing to the exit port of the casing;
a first optical window and a second optical window that are disposed at openings, exposed to the outside, of the first optical path tube and the second optical path tube, respectively; and
sealing materials that are disposed at the peripheries of the first and second optical windows to seal the first and second optical path tubes and have a water vapor transmission rate of 30000 cc·cm$^2$·mm·sec·cm Hg×$10^{10}$ or lower.

2. The cryostat according to item 1 above, wherein the largest diameters of the first and second optical windows are each 16 mm or larger.

3. The cryostat according to item 1 or 2 above, wherein the first and second optical path tubes contain an ethylene fluoride resin.

4. The cryostat according to any one of items 1 to 3 above, wherein the sealing materials contain a fluorine-containing polymer and/or a butyl rubber.

5. The cryostat according to item 4 above, wherein the fluorine-containing polymer is at least one member selected from a binary fluororubber and a ternary fluororubber.

6. The cryostat according to any one of items 1 to 5 above, further comprising an aperture window for restricting a light beam entering the first optical window.

7. The cryostat according to any one of items 1 to 6 above, further comprising a gas flow path for feeding a gas through the first optical path tube and/or the second optical path tube.

8. A circular dichroism spectrometer comprising the cryostat according to any one of items 1 to 7 above.

Advantageous Effects of Invention

The cryostat of the present invention uses a sealing material having a water vapor transmission rate of 30000 cc·cm$^2$·mm·sec·cm Hg×$10^{10}$ or lower as a sealing material for sealing the optical windows from the inside of the optical path tubes. This can prevent the entry of water vapor from outside, and effectively suppress water condensation on the surface of the cell. For example, even when measurement is performed under atmospheric pressure, water condensation on the surface of the cell can be effectively prevented. Therefore, the cryostat of the present invention need not be particularly provided with a mechanism for maintaining vacuum or the like, and its internal structure can thus be simplified. As a result, a reduction in the size of the cryostat can be realized. The cryostat of the present invention can prevent the entry of water vapor even when optical measurement is performed for a long period of time, and maintain significant effects in suppressing water condensation.

In the cryostat of the present invention, the diameters of the first optical window for allowing a light beam to enter the cell housing and/or the second optical window for allowing the light beam having passed through the cell housing to output are set to 16 mm or larger, and thus distortion in the optical windows due to heat and pressure can be prevented. As a result, optical measurement with high accuracy (for example, measurement of CD spectra) is facilitated.

Furthermore, the aperture window is placed outside the first optical window. Accordingly, incident light can be restricted, and optical measurement can be carried out more favorably.

Materials containing an ethylene fluoride resin are employed as the first and second optical path tubes within the cryostat of the present invention. Accordingly, moisture in the optical path tubes can be favorably removed, and water condensation on the surface of the cell can be further prevented.

A gas flow path is provided for feeding a gas to the first optical path tube and/or second optical path tube in the cryostat of the present invention. Accordingly, moisture inside the cryostat can be efficiently removed prior to the optical measurement. As a result, water condensation (fog) on the surface of the cell can be further prevented.

The cryostat of the present invention can be used as a cryostat for various optical measuring devices. In particular, the cryostat of the present invention can be favorably used as a cryostat for a circular dichroism spectrometer. According to the cryostat of the present invention, even when the cell is cooled to −80° C. or lower, for example, to about −165° C., water condensation on the surface of the cell can be effectively suppressed. Accordingly, a circular dichroism spectrometer comprising the cryostat of the present invention enables CD spectrum measurement at very low temperatures (for example, −165° C.).

In addition, since the cryostat of the present invention can prevent or suppress water condensation on the surface of the cell, it can favorably detect a CD spectrum in a short wavelength range, which has been difficult to measure. In addition, since the cryostat of the present invention can suppress distortion of the optical windows, it can detect a CD spectrum in a short wavelength range more reliably. It is observed that circularly polarized light in a short wavelength range is absorbed by many organic compounds and inorganic compounds. Since the cryostat of the present invention can favorably detect a CD spectrum in a short wavelength range, it can be used to determine the chirality of a much larger number of organic and inorganic compounds, compared to known cryostats. With the cryostat of the present invention, it is possible to establish a method for determining chirality that is more useful and general than conventional methods.

Mode for Carrying Out the Invention

An embodiment of the cryostat according to the present invention will be described below with reference to the drawings. FIG. 1 is a longitudinal cross-sectional view of a cryostat according to this embodiment.

It should be noted that in FIGS. 1 and 2, although a cryostat having three optical windows is shown, the cryostat of the present invention may have three or more optical windows, as long as the effects of the present invention are not impaired. For example, if the cryostat of the present invention is used for a spectrofluorimeter or a laser spectrometer, the cryostat preferably has three to five optical windows. When the cryostat has four or more optical windows, an optical path tube as will be described later is provided for each optical window, and sealing materials, which will be described below, for sealing the optical windows and the optical path tubes are disposed at the peripheries of the optical windows.

The cryostat in FIG. 1 has a rectangular casing 1, and a cell housing 2 disposed at the internal center thereof. A space between the inner wall face of the casing 1 and the cell housing 2 is filled with a heat insulating material 3, such as urethane foam.

The casing 1 is formed of a plastic, metal (for example, aluminum alloy) or the like, and an opening is formed on each of its opposing side faces and the top face. The cell housing 2 is similarly formed in a rectangular shape, and openings are formed in the positions opposing the openings of the casing 1, respectively. As will be described later, in the casing 1 and cell housing 2, each of the openings formed on the left in FIG. 1 forms an inlet port from which a light beam enters, and each of the openings formed on the right forms an exit port.

In addition, the casing 1 and an opening 6 formed on the top face of the cell housing 2 are connected via a tube member 7, through which a sample is placed from the top face of the casing 1 into the cell housing 2.

On the wall faces of the cell housing 2, passages forming the inlet port and exit port are each formed by a small-diameter portion that is exposed on the outside, and a large-diameter portion that is exposed on the inside. Herein, the small-diameter portion formed at the inlet port is referred to as a light inlet 4; one of the large-diameter portions as a first cavity 8; the small-diameter portion formed at the exit port as a light outlet 5; and the other large-diameter portion as a second cavity 9. With the first cavity 8 as mentioned above, water condensation in a portion of the surface of the cell that is irradiated with a light beam can be dispersed. Meanwhile, with the second cavity 9, the cell is exposed in a range larger than a portion of the surface of the cell where the light beam passes through, and therefore water condensation in the portion of the surface of the cell where the light beam passes through can be dispersed. At this time, the largest diameters of the first and second cavities (the diameters, if the first and second cavities are cylindrical) are preferably 12 mm or larger, and more preferably 14 to 20 mm.

The bore sizes of the light inlet 4 and light outlet 5 formed on the cell housing are not particularly limited, but are preferably 2 to 20 mm.

In addition, the wall face of the cell housing 2 is formed by a heating/cooling block 10 that has a heating/cooling pipe (not shown, temperature control means) thereinside, and the temperature of the cell can be adjusted by this heating/cooling pipe. Specifically, the cell can be cooled to a very low temperature (for example, −80° C. or lower) by feeding liquid nitrogen through the heating/cooling pipe, while the cell can be heated to 100° C. or higher by feeding constant temperature water and the like. The heating/cooling pipe runs from the heating/cooling block 10 to the outside of the casing 1, and has an inlet (not shown) for feeding liquid nitrogen or the like.

A heater may be included in the heating/cooling block. The cell can be heated by the heater.

The capacity of the cell housing 2 is not particularly limited. For example, it can be suitably set such that a cell measuring 1 to 50 mm in length, 1 to 50 mm in width, and 10 to 100 mm in height can be accommodated in the cell housing 2.

As shown in FIG. 1, the opposing inlet ports formed on the side faces of the casing and the cell housing are connected to each other by the optical path tube; their opposing exit ports are similarly connected to each other. That is, the inlet ports on the left in FIG. 1 are connected to each other by the first optical path tube 11, while the exit ports on the right side in FIG. 1 are connected to each other by the second optical path tube 12.

The first optical path tube is composed of a first tube portion 13 passing through the casing 1, and a second tube portion 14 extending to the outside of the casing and having a diameter larger than that of the first tube portion 13. In addition, a first optical window 15 is attached to the second tube portion 14, and a light beam entering from this optical window is led into the cell housing 2 via the first optical path tube 11. The second optical path tube 12 is also formed in a manner similar to the first optical path tube 11. That is, the second optical path tube 12 is composed of a first tube portion 16 having a small diameter, and a second tube portion 17 having a large diameter. In addition, the second tube portion 17 disposed outside the casing 1 is provided with a second optical window 18, and a light beam that has passed through the cell housing 2 is outputted to the outside from the second optical window 18 via the second optical path tube 12. As for the first and second optical windows, the sealing materials 19 are disposed at the peripheries of the faces facing the casing 1, respectively, and the optical path tubes are sealed by the optical windows and the sealing materials. According to the constitution described above, the first optical window 15, first optical path tube 11, cell housing 2, second optical path tube 12, and second optical window 18 are disposed on a straight line, which allows a light beam to pass along this straight line.

The shapes of the first and second optical windows are not particularly limited, and may be, for example, round, elliptic, and the like. In particular, in the cryostat of this embodiment, the shapes of the optical windows are preferably round. The round shape allows a light beam to enter the cryostat favorably. In addition, the largest diameters (the diameters, if the optical windows are round) of the optical windows are preferably 16 mm or larger, and more preferably 20 to 30 mm. When the largest diameter is 16 mm or larger, the distortion of the optical windows due to heat and pressure can be effectively suppressed. When the largest diameter is 16 mm or larger, a light beam can be favorably led into the cell housing 2. When the largest diameter is smaller than 16 mm, distortion of the optical windows may be caused by heat and pressure. In such a case, the problem that CD spectra cannot be accurately measured and other inconveniences may occur. The thickness of each optical window may be about 0.2 to 10 mm.

In addition, an aperture window 20 for restricting a light beam entering the first optical window 15 is provided on the face of the first optical window 15 that faces the outside. For example, if the size of the first optical window is 16 mm or larger, the opening portion is adjusted so that the diameter of the opening portion of the aperture window 20 is 10 mm or smaller, and preferably 9 to 2 mm, whereby the distortion of the optical windows can be effectively suppressed; and at the same time a light beam can favorably enter the cryostat.

Furthermore, the cryostat is provided with a gas flow path (not shown) for feeding a dry gas to the first optical path tube 11, the second optical path tube 12, and a third optical path tube 21, which will be described later.

Subsequently, the materials that form the above cryostat will be described.

The optical windows may be, for example, those made of $CaF_2$, LiF, $MgF_2$, $BaF_2$, TlBrI, TlBrCl, NaCl, KBr, KCl, $SiO_2$, CsI, ZnSe, and the like.

The optical path tubes may be similar to those used for previously known cryostats without any limitation; however, those containing an ethylene fluoride resin are preferable. The ethylene fluoride resin contained therein can favorably remove moisture in the optical path tubes. As a result, water condensation on the surface of the cell can be further suppressed.

Examples of the ethylene fluoride resin include ethylene monofluoride resins, ethylene difluoride resins, ethylene trifluoride resins, and tetrafluoroethylene resins. These ethylene fluoride resins may be used singly, or in a combination of two or more. Among these, ethylene trifluoride resins are particularly preferable.

The above-described sealing material characteristically has a water vapor transmission rate of 30000 $cc \cdot cm^2 \cdot mm \cdot sec \cdot cm\ Hg \times 10^{10}$ or lower. It should be noted that the water vapor volume cc in this specification means a water vapor volume at STP (normal atmospheric pressure, 0° C.). Preferable examples of such a sealing material include those that contain polychloroprene, natural rubber, isoprene rubber, chlorosulfonated polyethylene rubber, styrene butadiene rubber, ethylene-propylene rubber, nitrile rubber (polybutadiene acrylonitrile), chlorosulfonated polyethylene, polyurethane, epichlorohydrin rubber, fluorine-containing polymers, butyl rubber, and the like (hereinafter also referred to as "gas blocking materials"). In particular, the fluorine-containing polymer and butyl rubber have a water vapor transmission rate of 2000 $cc \cdot cm^2 \cdot mm \cdot sec \cdot cm\ Hg \times 10^{10}$ or lower (preferably, 2000 to 3 $cc \cdot cm^2 \cdot mm \cdot sec \cdot cm\ Hg \times 10^{10}$), and are highly effective in preventing the entry of moisture from outside. That is, in the present invention, it is preferable to use a sealing material that contains a fluorine-containing polymer and/or butyl rubber. With the use of a sealing material containing the fluorine-containing polymer and/or butyl rubber for sealing the optical windows, the entry of moisture from outside can be effectively suppressed. In particular, the fluorine-containing polymer is favorable in terms of its chemical resistance, such as resistance to organic solvents (for example, resistance to methanol).

Examples of the fluorine-containing polymer include binary fluororubbers, ternary fluororubbers, and the like.

Examples of the binary fluororubbers include tetrafluoroethylene propylene-hexafluoride copolymers, vinylidene fluoride-hexafluoropropylene copolymers, tetrafluoroethylene perfluoro(alkyl vinyl ether) copolymers, and the like.

Examples of the ternary fluororubbers include vinylidene fluoride-tetrafluoroethylene perfluoro(alkyl vinyl ether) copolymers, vinylidene fluoride-hexafluoropropylene-tetrafluoroethylene copolymers, vinylidene fluoride-propylene-tetrafluoroethylene copolymers, perfluoro(alkyl vinyl ether)-ethylene-tetrafluoroethylene copolymers, and the like.

These fluororubbers may be used singly, or in a combination of two or more. The exemplary fluororubbers described above may be any of block copolymers, random copolymers, alternating copolymers, and graft copolymers. In addition, the proportion of each monomer component in the copolymers is not particularly limited, and may be any proportion as long as the effect in preventing the entry of water vapor by the sealing material can be sufficiently exhibited.

In particular, for example, "Dyneon LTFE 6400X" (product name; manufactured by Sumitomo 3M Limited) is preferable as the fluororubber in terms of its excellent chemical resistance, heat resistance, and the like.

When the sealing material contains a fluorine-containing polymer and/or butyl rubber, the amount of the fluorine-containing polymer and/or butyl rubber contained in the sealing material is preferably 50% by weight or more, and more preferably 60 to 80% by weight. When the sealing material contains the fluorine-containing polymer and/or butyl rubber, and the amount of the fluorine-containing polymer and/or butyl rubber contained is lower than 50% by weight, the sealing material may fail to prevent the entry of water vapor into the cryostat.

The sealing material may contain, if necessary, additives that are generally used for sealing materials, such as organic peroxides, cross-linking aids, fillers, processing aids, and acid-accepting agents. These may be used singly, or in a combination of two or more.

Examples of the organic peroxide include di-tert-butyl peroxide, dicumyl peroxide, tert-butyl cumyl peroxide, 1,1-di(tert-butylperoxy)-3,3,5-trimethylcyclohexane, 2,5-dimethyl-2,5-di(tert-butylperoxy)hexane, 2,5-dimethyl-2,5-di(tert-butylperoxy)hexyne-3, 1,3-di(2-tert-butylperoxy isopropyl)benzene, 2,5-dimethyl-2,5-di(benzoylperoxy)hexane, tert-butyl peroxybenzoate, tert-butylperoxy isopropyl carbonate, n-butyl-4,4-di(tert-butylperoxy)valerate, and the like. These may be used singly, or in a combination of two or more kinds.

Although the amount of the organic peroxide contained in the sealing material is not particularly limited, the amount is preferably 0.5 to 10 parts by weight, and more preferably 1 to 5 parts by weight, per 100 parts by weight of the gas-blocking material.

Examples of the cross-linking aid include polyfunctional unsaturated compounds. Examples of the polyfunctional unsaturated compound include triallyl isocyanurate, triallyl cyanurate, diallyl phthalate, trimethallyl isocyanurate, 1,3-butylene glycol dimethacrylate, 1,4-butylene glycol dimethacrylate, ethylene glycol dimethacrylate, diethylene glycol dimethacrylate, triethylene glycol dimethacrylate, tetraethylene glycol dimethacrylate, trimethylolpropane triacrylate, trimethylolpropane trimethacrylate, and the like. These may be used singly, or in a combination of two or more.

The amount of the cross-linking aid contained in the sealing material is preferably 0.1 to 20 parts by weight, and more preferably 1 to 10 parts by weight, per 100 parts by weight of the gas blocking material.

Examples of the filler include mica, talc, clay, graphite, silicic acid, and the like. These may be used singly, or in a combination of two or more kinds. The amount of the filler contained in the sealing material is not particularly limited as long as the functions of the sealing material are not impaired.

Examples of the processing aid include stearic acid, stearylamine, paraffin wax, and the like. These may be used singly, or in a combination of two or more kinds. The amount of the processing aid contained in the sealing material is not particularly limited, and may be suitably adjusted depending on the target sealing material.

Examples of the acid-accepting agent include zinc oxide, magnesium oxide, and the like. These may be used singly, or in a combination of two or more kinds. The amount of the acid-accepting agent contained in the sealing material is not particularly limited, as long as the effects of the present invention are not impaired.

In addition, thermal carbon black, cross-linking agents, lubricants, and the like may be contained in the sealing material.

The sealing material can be prepared, for example, by kneading the respective components of the gas-blocking material using kneaders such as an Intermix, a kneader, and a Banbury mixer; or an open roll mill.

When the sealing material is prepared, the gas-blocking material in the sealing material may be made to crosslink, if necessary.

Examples of the cross-linking method include those that employ heating by using an injection molding machine, a compression molding machine, a vulcanizing press, and the like. The heating temperature is preferably 100 to 250° C., and more preferably 150 to 200° C. The heating time is preferably 1 to 60 minutes.

The state of the sealing material is not particularly limited, and may be a paste or a solid. Particularly in the present invention, a sealing material processed into an O-ring is preferably used. By using a sealing material processed into an O-ring as the sealing material, the entry of moisture can be further suppressed.

In the cryostat of the present invention, a cell 27 is placed in the cell housing 2, and cooled by the heating/cooling block 10; and a light beam (524 nm) is emitted and enters the first optical window 15, and is irradiated onto the cell 27 via the first optical path tube 11, light inlet 4, and first cavity 8. The light beam then passes through the cell 27, and exits from the second optical window 18 via the second cavity 9, light outlet 5, and second optical path tube 12.

Feeding of a dry gas after installation of the cell prior to optical measurement enables effective removal of moisture inside the cryostat. Examples of the dry gas include nitrogen, argon, and the like. These dry gases can be used singly, or in a combination of two or more.

The fed dry gas flows through the gap between the cell 27 and the heating/cooling block 10, and is discharged from the opening 6.

While one embodiment of the present invention has been described above, the present invention is not limited to the above embodiment, and various changes may be made so far as they do not deviate from the spirit of the invention. For example, a passage for allowing a fluorescence light beam to emit from the cell housing 2 can be formed in the above cryostat. More specifically, as shown in FIG. 2, a fluorescence light exit port 23 is formed on a side face of the cell housing 2 that is perpendicular to the side faces on which the inlet port 4 and exit port 5 are formed. The constitution of this fluorescence light exit port 23 is similar to those of the inlet port 4 and exit port 5, and a third cavity with a large diameter (not shown) is formed at the fluorescence light exit port 23. Therefore, water condensation in the portion of the surface of the cell through which the fluorescence light beam passes can be dispersed. In addition, in the casing 1, a similar fluorescence light exit port is provided in a position opposing the fluorescence light exit port 23, and these fluorescence light exit ports are connected by the third optical path tube 21. The third optical path tube 21 has the same constitution as the first and second optical path tubes. That is, the third optical path tube 21 is constructed of the first tube portion having a small diameter 24, and the second tube portion having a large diameter 25. In addition, a third optical window 26 and a sealing material 19 are disposed in a second tube portion 25, which is a part of the third optical path tube 21 and extends to the outside of the casing 1. These constitutions are also similar to the optical windows and sealing materials described above. The bore size of the fluorescence light exit port 23 is not particularly limited, but is preferably 2 to 30 mm.

Such a structure also allows measurement of the fluorescence light emitted from the sample.

In addition, the above first cavity 8 and second cavity 9 may be formed independently of each other, or may be integrally formed. For example, when they are integrally formed, forming a groove extending in the circumferential direction along the inner wall face of the cell housing allows both cavity portions to be integrally formed. In addition, the same applies to the third cavity (not shown), and the three cavities may be formed separately or integrally.

The cryostat as mentioned above can be used as a cell chamber for various optical measuring devices, such as circular dichroism spectrometers and ultraviolet-visible spectrophotometers. In particular, the cryostat of the present invention can be favorably used as a cryostat for circular dichroism spectrometers. In particular, when it is used as a cell chamber in a circular dichroism spectrometer, the circular dichroism spectrometer can favorably measure CD spectra at an even lower temperature (for example, −100° C. or lower) than conventional circular dichroism spectrometers.

It should be noted that components of the circular dichroism spectrometer other than the cryostat may be the same as those of conventional circular dichroism spectrometers.

EXAMPLES

Examples and Comparative Examples will be shown below to more specifically describe the present invention. However, the present invention is not limited to the Examples.

Example 1

A cryostat having the structure shown in FIG. 1 was assembled.

A composition containing the components described in Table 1 below was used for a sealing material 19.

TABLE 1

| | |
|---|---|
| Fluorine-containing polymer (product name "Dyneon LTFE 6400X", manufactured by Sumitomo 3M Limited) | 100 g |
| Thermal carbon black N990 (MT Carbon) | 50 g |
| Zinc oxide | 5 g |
| Peroxide (product name "DBPH-50"; manufactured by Varox) | 2.5 g |
| Cross-linking agent (manufactured by TAIC; 72%) | 2.5 g |
| Lubricant (product name "WS 280"; manufactured by Struktol) | 0.5 g |

The water vapor transmission rate of the above fluorine-containing polymer (Dyneon LTFE 6400X) is 520 cc·cm$^2$·mm·sec·cm Hg×10$^{10}$.

The diameters of the light inlet 4, light outlet 5, first optical path tube 11, second optical path tube 12, and fluorescence light exit port 23 provided in the heating/cooling block 10 were all 10 mm.

The first optical window 15, second optical window 18, and third optical window 26 used were all made of synthetic quartz, and had a round shape and a diameter of 25 mm.

The first optical path tube 11, second optical path tube 12, and third optical path tube 21 used were all made of "Daiflon" (product name; manufactured by Daikin Industries Limited) containing an ethylene trifluoride resin.

The cell 27 used was made of synthetic quartz (size: optical path length 1 cm, width 1 cm, capacity 4 cm$^3$).

Comparative Example 1

A cryostat was assembled in a manner similar to that in Example 1, except that silicon was used as the sealing material 19. The water vapor transmission rate of silicon is 106000 cc·cm$^2$·mm·sec·cm Hg×10$^{10}$.

Example 2

A cryostat having the structure shown in FIGS. 3 and 4 was assembled.

More specifically, a cryostat was assembled in a manner similar to those in FIGS. 1 and 2, except that the diameters of the first optical window 15, second optical window 18, and third optical window 26 were all 15 mm; the aperture window 20 was not provided; the diameters of the first cavity 8, second cavity 9, and third cavity (not shown) were all 18 mm; and the gas flow path 22 was not provided.

Comparative Example 2

A cryostat was assembled in a manner similar to that in Example 2, except that silicon was used as the sealing material 19.

Example 3

A cryostat having the structure shown in FIGS. 5 and 6 was assembled.

Specifically, a cryostat similar to those in FIGS. 3 and 4 was assembled, except that the diameters of the first cavity 8, second cavity 9, and third cavity (not shown) were all 8 mm.

Comparative Example 3

A cryostat was assembled in a manner similar to that in Example 3, except that silicon was used as the sealing material 19.

Example 4

A cryostat having the structure shown in FIGS. 7 and 8 was assembled.

Specifically, a cryostat similar to those in FIGS. 1 and 2 was assembled, except that the diameters of the first optical window 15, second optical window 18, and third optical window 26 were all 15 mm.

Comparative Example 4

A cryostat having the structure shown in FIGS. 9 and 10 was assembled.

Specifically, a cryostat similar to that of Comparative Example 2 was assembled, except that the diameters of the first optical window 15, second optical window 18, and third optical window 26 were all 25 mm.

Example 5

A cryostat was assembled in a manner similar to that in Example 1, except that a butyl rubber was used in place of the fluorine-containing polymer. The water vapor transmission rate of the butyl rubber is 400 to 2000 cc·cm$^2$·mm·sec·cm Hg×10$^{10}$.

Example 6

A cryostat was assembled in a manner similar to that in Example 1, except that the diameters of the light inlet 4, light outlet 5, first optical path tube 11, second optical path tube 12, and fluorescence light exit port 23 provided in the heating/cooling block 10 were all 8 mm.

Example 7

A cryostat was assembled in a manner similar to that in Example 1, except that polychloroprene was used as the sealing material 19. The water vapor transmission rate of polychloroprene is 18000 cc·cm$^2$·mm·sec·cm Hg×10$^{10}$.

Test Example 1

The cell 27 made of glass (size: optical path length 1 cm, width 1 cm, capacity 4 cm$^3$) containing 4 cm$^3$ of ethyl alcohol was placed into the cell housing 2 of each of the cryostats assembled in Examples 1 to 7 and Comparative Examples 1 to 4, and the opening 6 on the upper face of the casing 1 was closed with a lid (not shown).

Next, liquid nitrogen was poured from an inlet on the surface of the casing 1, and fed through the heating/cooling pipe in the heating/cooling block 10, whereby the cell 27 was cooled (temperature of the cell: −80° C.).

Subsequently, a light beam (524 nm) was emitted through the first optical window 15. The light beam was irradiated onto the cell 27 via the first optical path tube 11, light inlet 4, and first cavity 8. The light beam then passed through the cell 27, and exited from the second optical window 18 via the second cavity 9, light outlet 5, and second optical path tube 12.

It should be noted that in Examples 1, 5, 6, and 7; and Comparative Example 1 and Example 4, the opening 6 on the upper face of the casing 1 was closed with a lid, and then argon was poured into the gas flow path 22 prior to pouring liquid nitrogen.

The gas poured flowed through the gap between the cell 27 and the heating/cooling block 10, and was discharged from the opening 6.

The measurement results of absorbance are shown in FIGS. 11 to 20, and 22.

Test Example 2

CD spectra were measured using the cryostat assembled in Example 1 in place of a standard cell holder installed in a circular dichroism spectrometer "J-820" (product name; manufactured by JASCO Corporation).

In the measurement, the cell was cooled to a temperature of −140° C. The CD spectra obtained are shown in FIG. 21. In FIG. 21, the CD spectra when the temperature of the cell was 25° C., −10° C., −40° C., −80° C., and −110° C. are further shown.

In addition, in FIG. 21, the UV spectra and spectra with anisotropy factor (g factor) measured under similar temperature conditions are shown together.

The g factor can be calculated by dividing $\Delta\epsilon$, determined from the CD spectrum in FIG. 21, by $\epsilon$, determined from the UV spectrum in FIG. 21.

Figure 1:
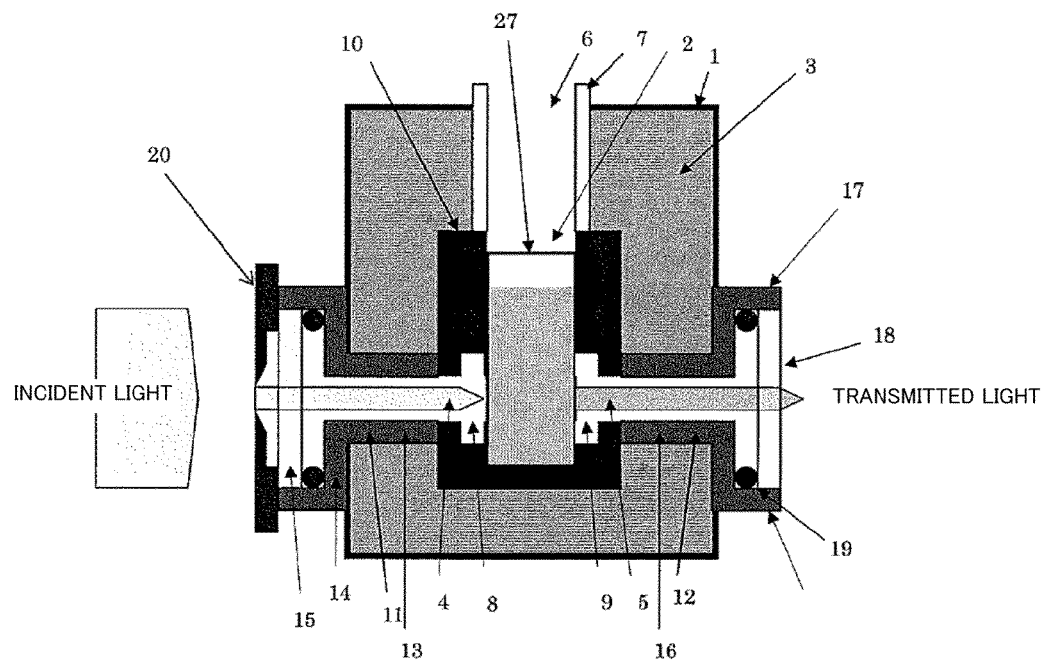
FIG. 1 is a longitudinal cross-sectional view of a cryostat assembled in Examples 1, 5, and 6, and Comparative Example 1.
Figure 2:
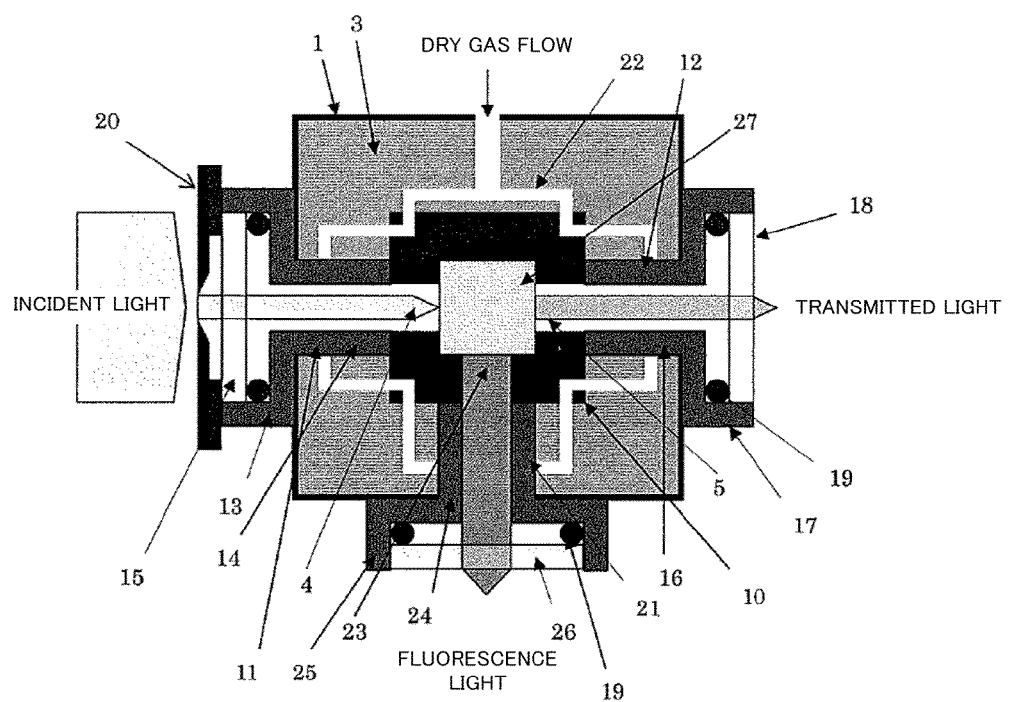
FIG. 2 is a transverse cross-sectional view of the cryostat assembled in Example 1 and Comparative Example 1.
Figure 3:
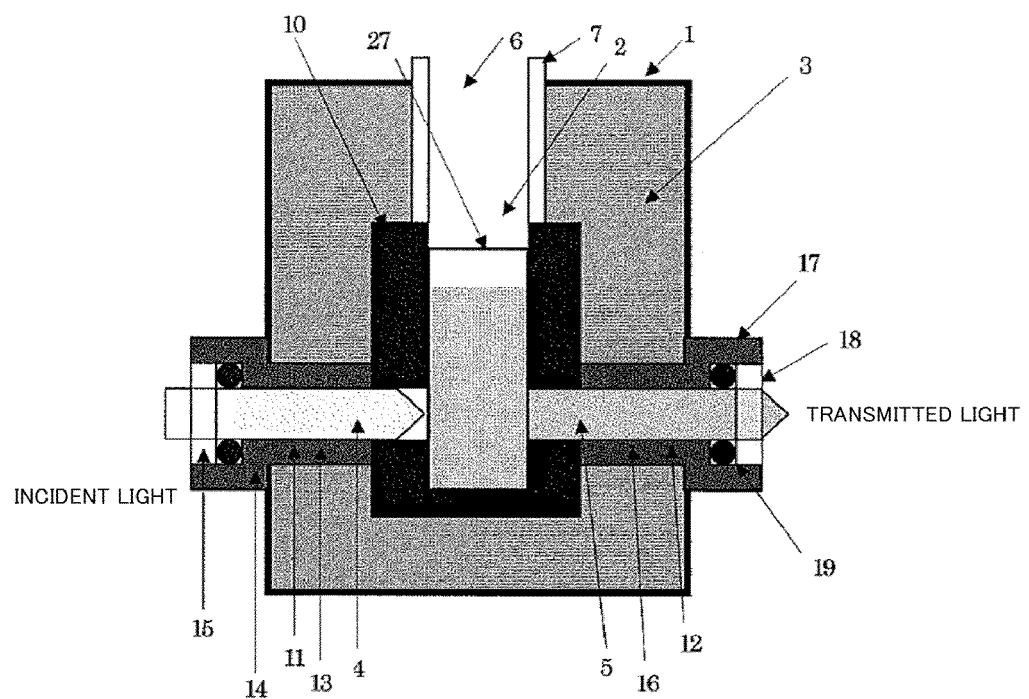
FIG. 3 is a longitudinal cross-sectional view of a cryostat assembled in Example 2 and Comparative Example 2.
Figure 4:
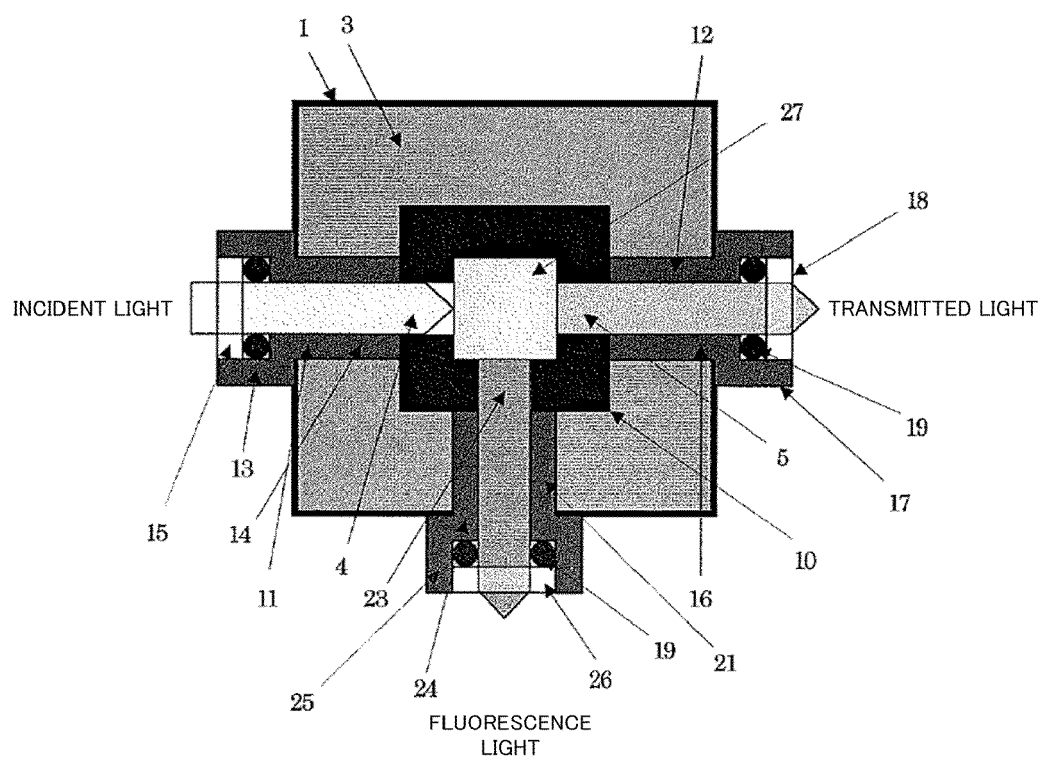
FIG. 4 is a transverse cross-sectional view of the cryostat assembled in Example 2 and Comparative Example 2.
Figure 5:
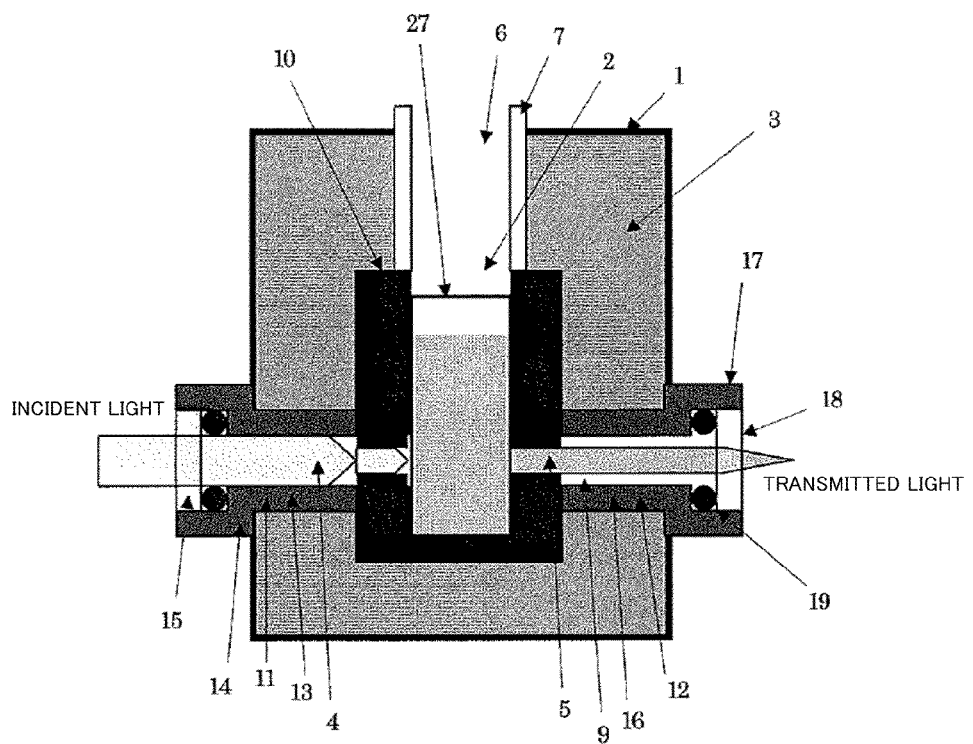
FIG. 5 is a longitudinal cross-sectional view of a cryostat assembled in Example 3 and Comparative Example 3.
Figure 6:
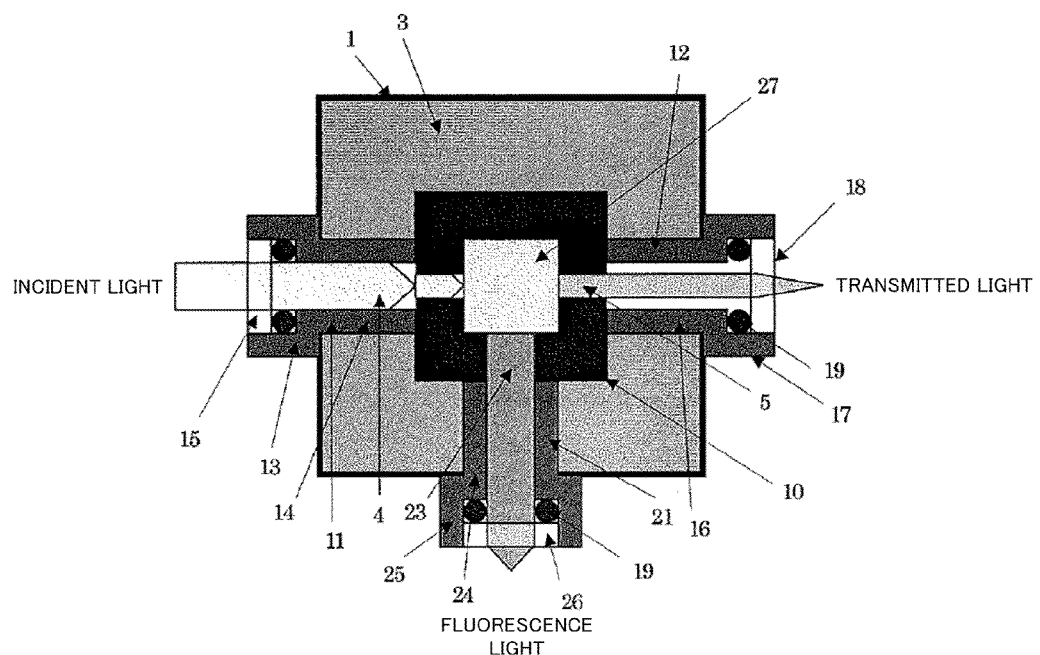
FIG. 6 is a transverse cross-sectional view of the cryostat assembled in Example 3 and Comparative Example 3.
Figure 7:
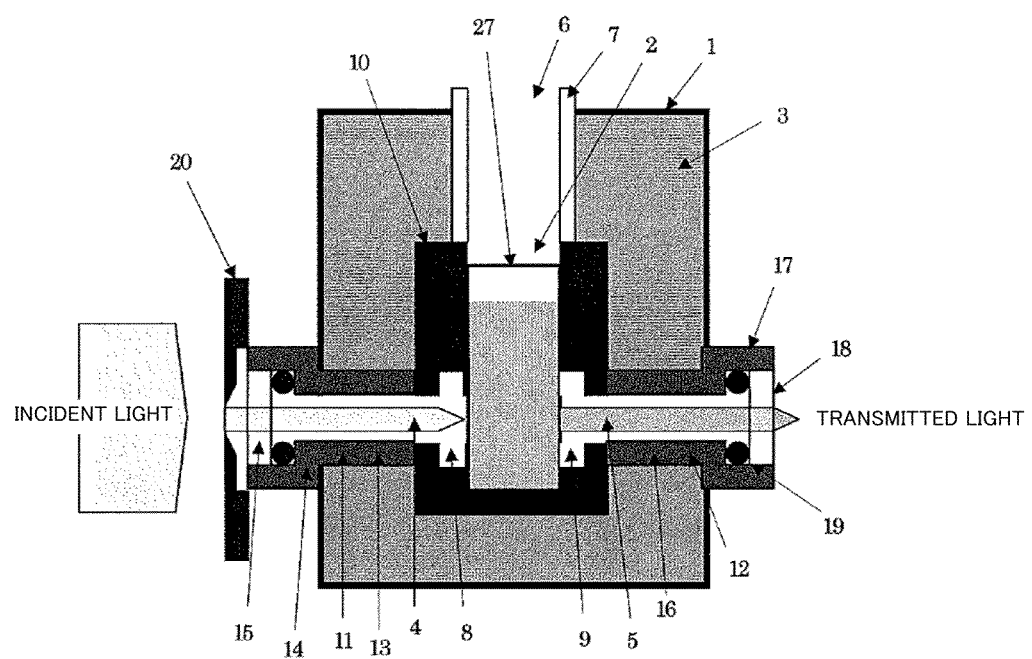
FIG. 7 is a longitudinal cross-sectional view of a cryostat assembled in Example 4.
Figure 8:
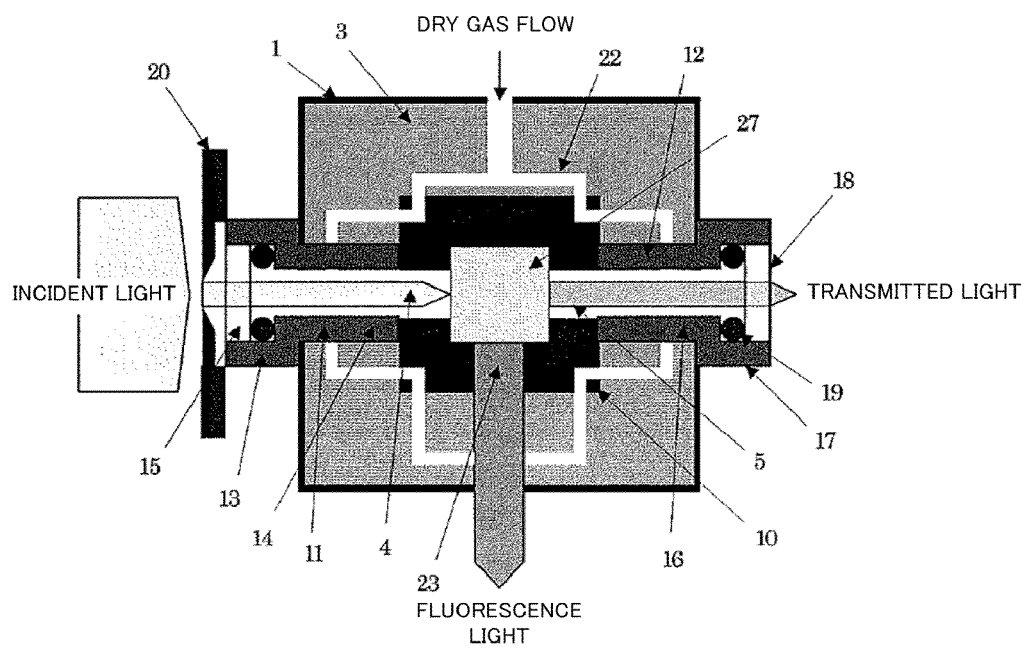
FIG. 8 is a transverse cross-sectional view of the cryostat assembled in Example 4.
Figure 9:
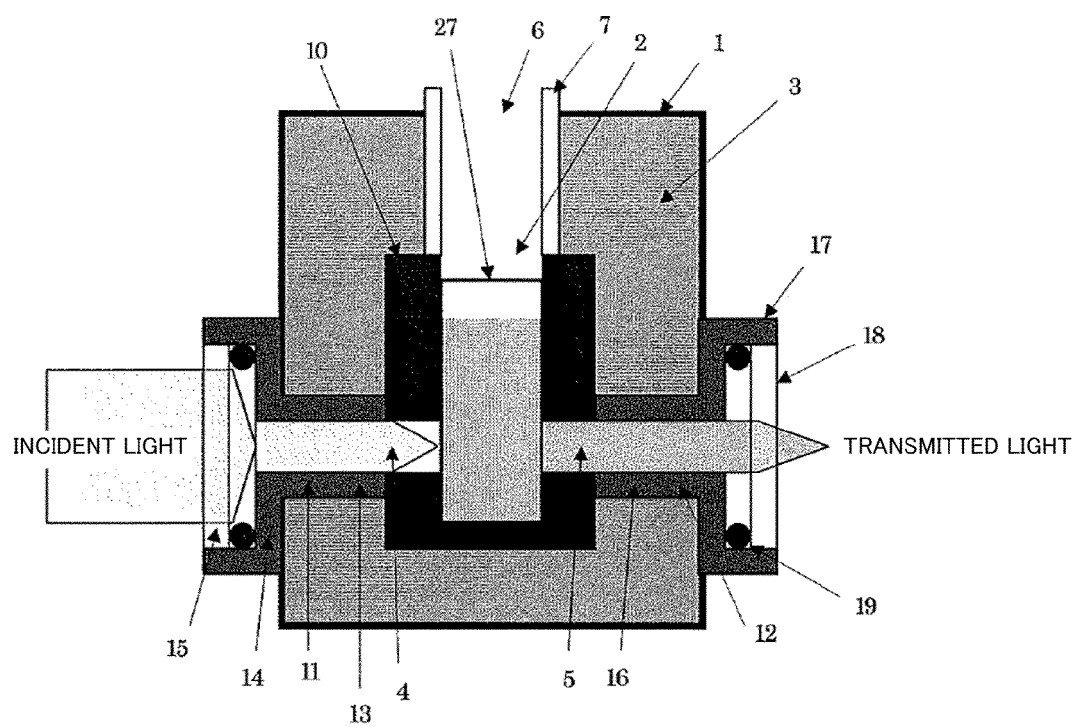
FIG. 9 is a longitudinal cross-sectional view of a cryostat assembled in Comparative Example 4.
Figure 10:
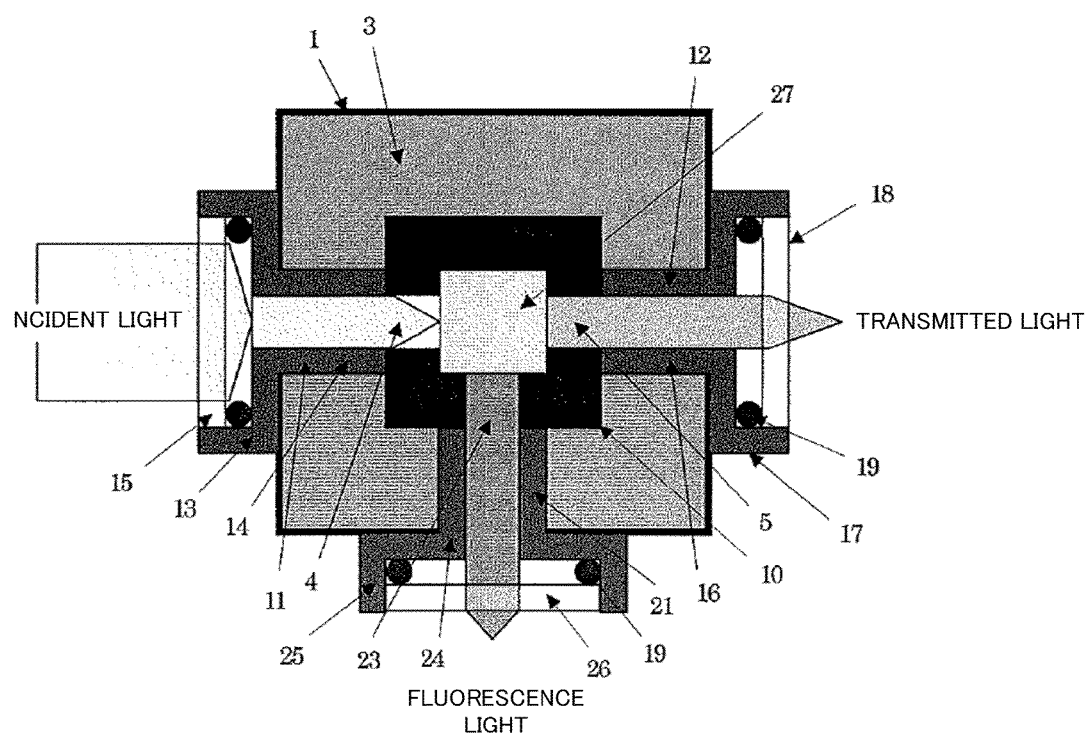
FIG. 10 is a transverse cross-sectional view of the cryostat assembled in Comparative Example 4.
Figure 11:
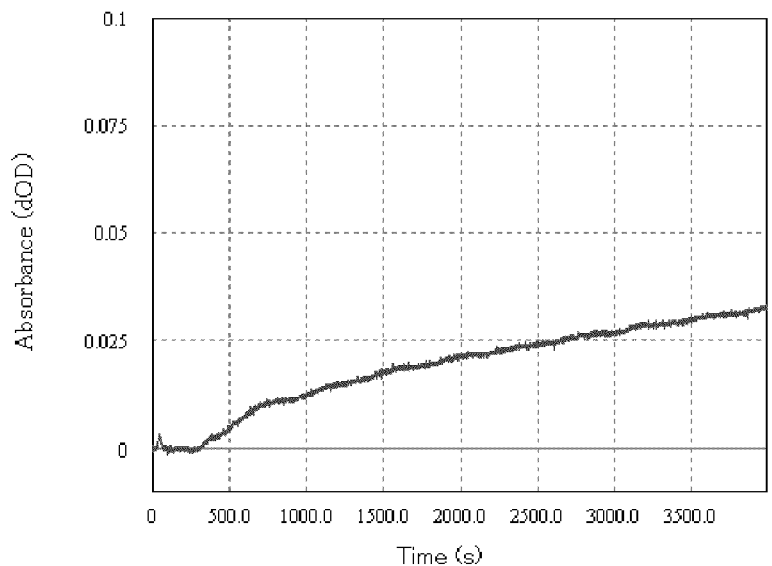
FIG. 11 is a graph showing measurement results of absorbance when the cryostat assembled in Example 1 was used.
Figure 12:
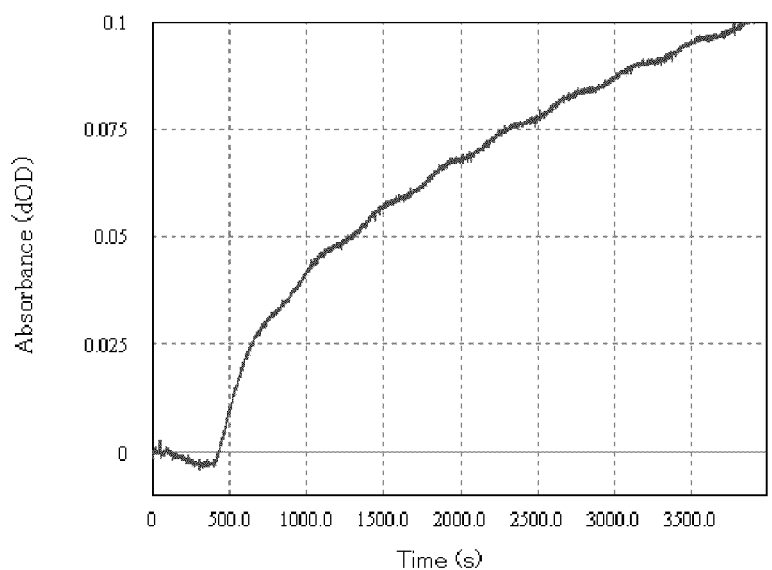
FIG. 12 is a graph showing measurement results of absorbance when the cryostat assembled in Comparative Example 1 was used.
Figure 13:
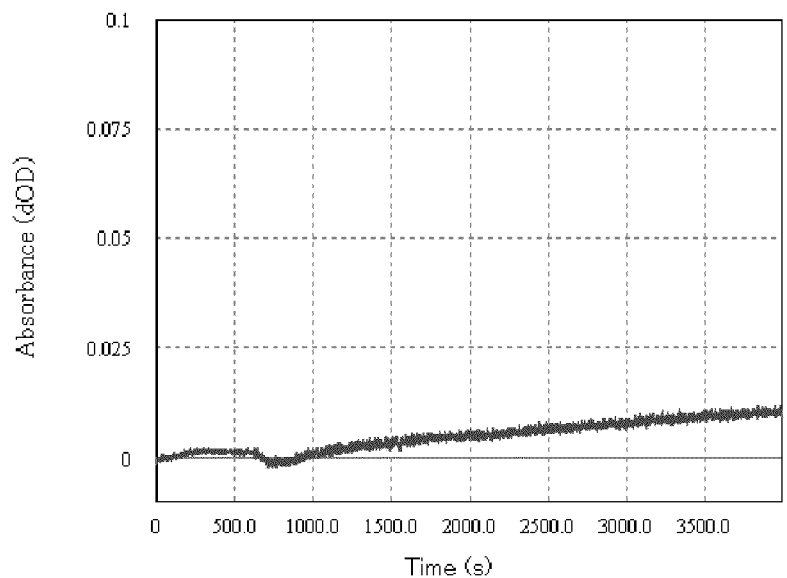
FIG. 13 is a graph showing measurement results of absorbance when the cryostat assembled in Example 2 was used.
Figure 14:
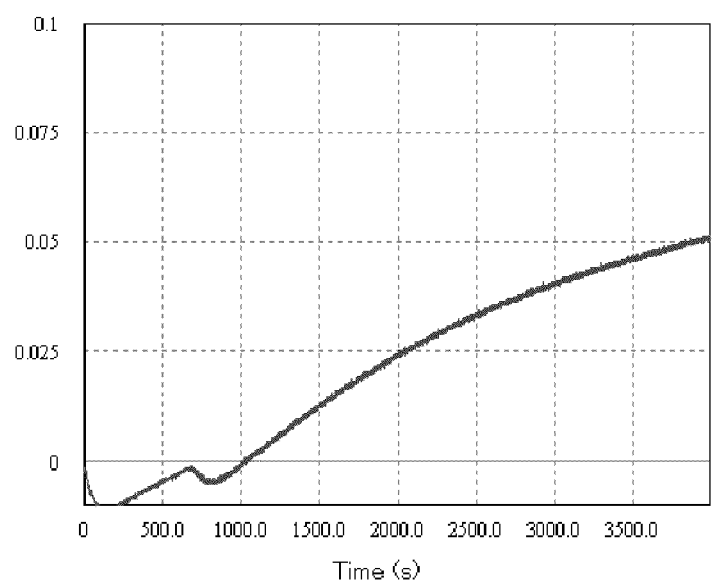
FIG. 14 is a graph showing measurement results of absorbance when the cryostat assembled in Comparative Example 2 was used.
Figure 15:
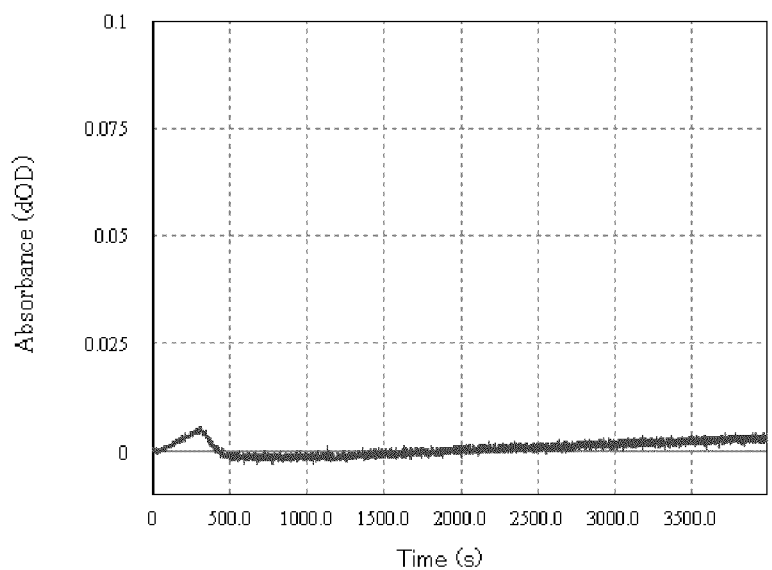
FIG. 15 is a graph showing measurement results of absorbance when the cryostat assembled in Example 3 was used.
Figure 16:
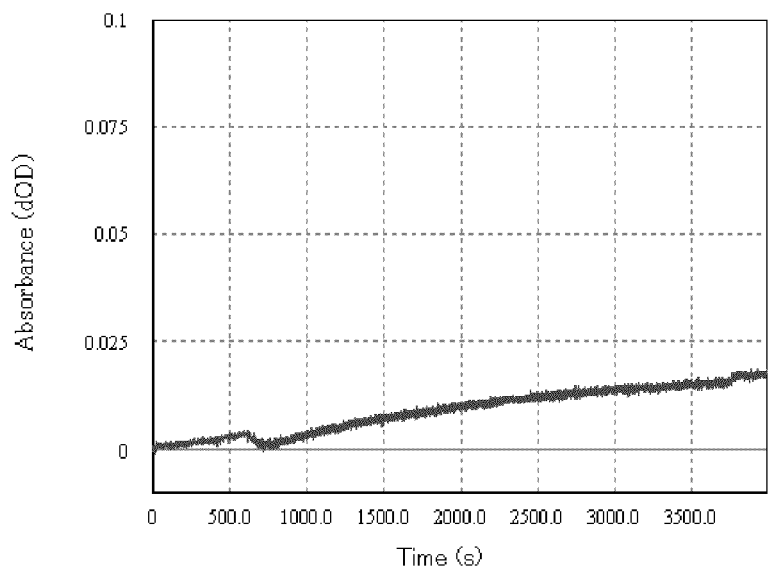
FIG. 16 is a graph showing measurement results of absorbance when the cryostat assembled in Comparative Example 3 was used.
Figure 17:
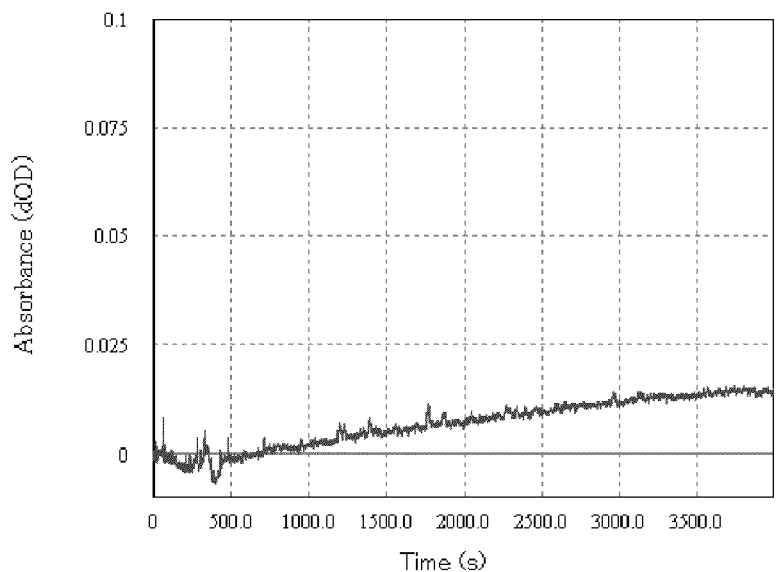
FIG. 17 is a graph showing measurement results of absorbance when the cryostat assembled in Example 4 was used.
Figure 18:
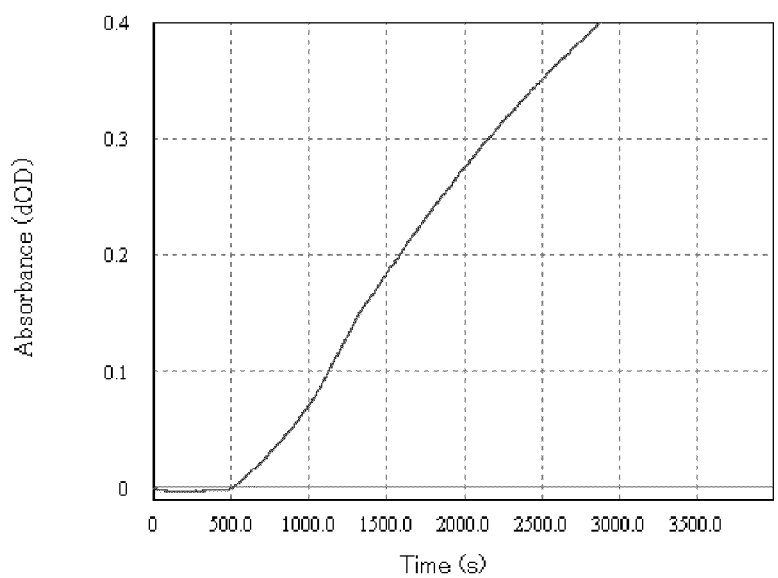
FIG. 18 is a graph showing measurement results of absorbance when the cryostat assembled in Comparative Example 4 was used.
Figure 19:
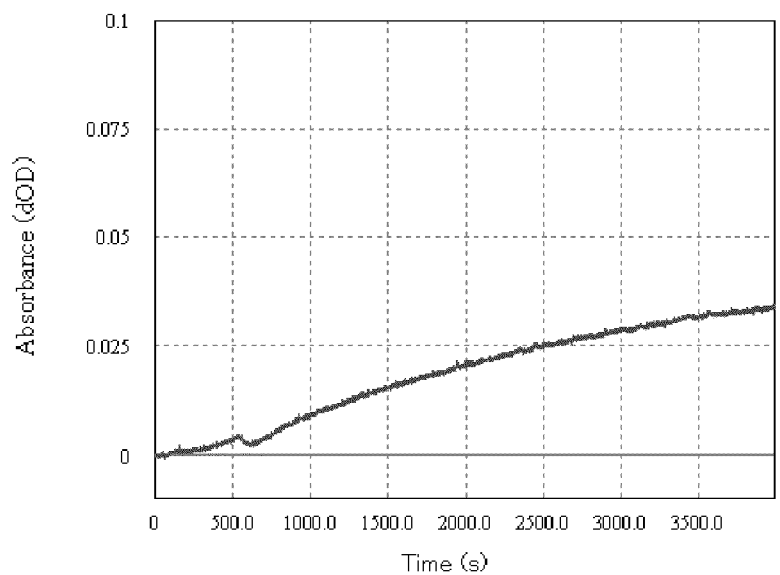
FIG. 19 is a graph showing measurement results of absorbance when the cryostat assembled in Example 5 was used.
Figure 20:
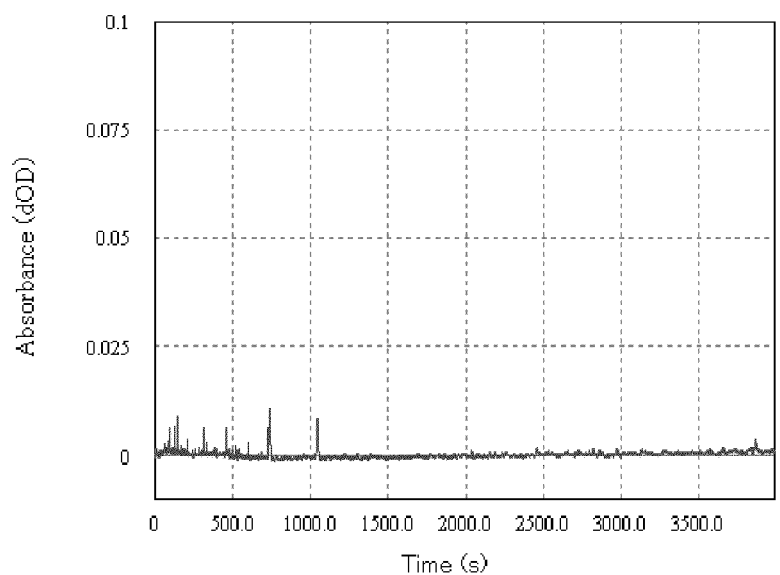
FIG. 20 is a graph showing measurement results of absorbance when the cryostat assembled in Example 6 was used.
Figure 21:
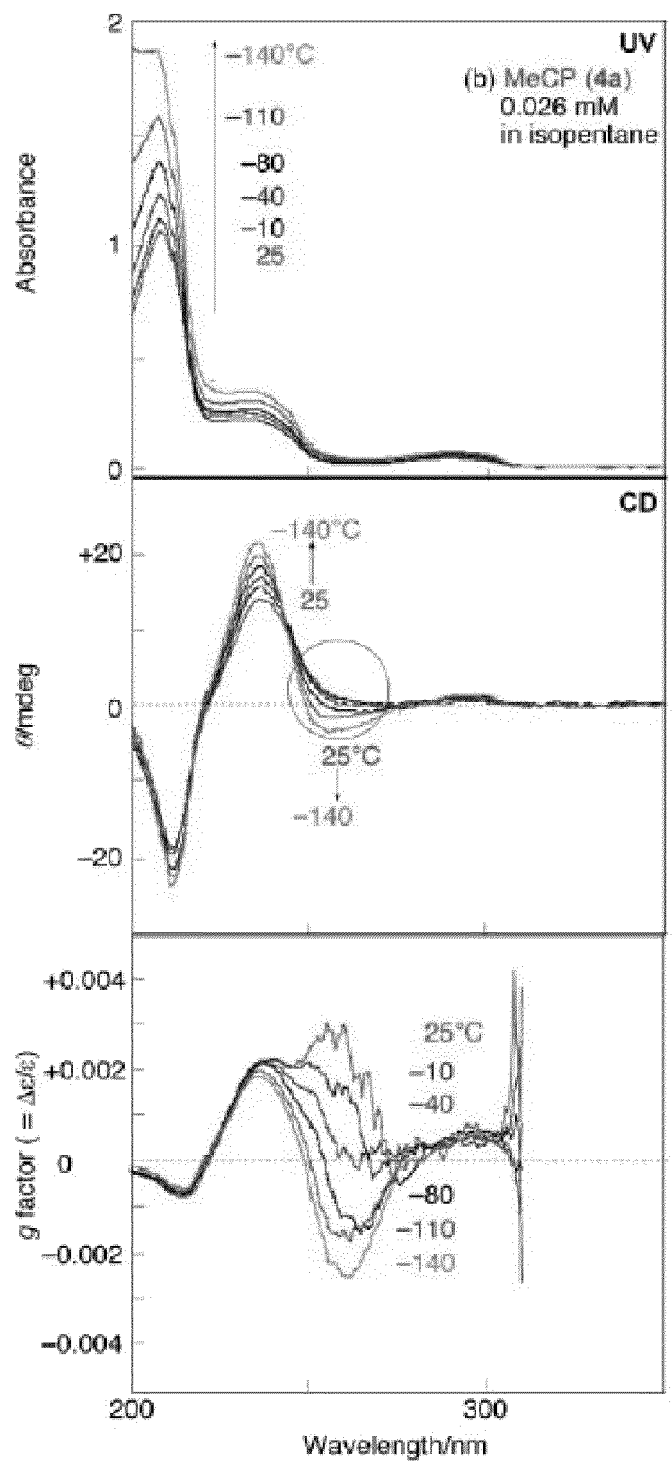
FIG. 21 is a graph showing CD spectra, UV spectra, and the g-factor spectra measured in Test Example 2.
Figure 22:
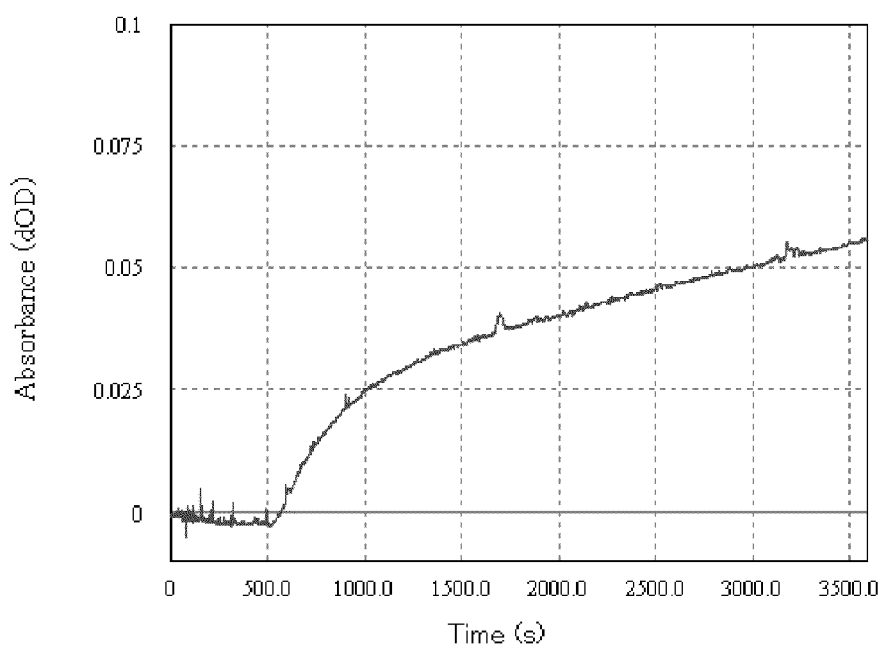
FIG. 22 is a graph showing measurement results of absorbance when the cryostat assembled in Example 7 was used.

REFERENCE NUMERAL LIST 1. casing
2. cell housing
3. heat insulating material
4. light inlet
5. light outlet
6. opening
7. tube member
8. first cavity
9. second cavity
10. heating/cooling block
11. first optical path tube
12. second optical path tube
13. first tube portion of first optical path tube (having a diameter smaller than the second tube part)
14. second tube portion of first optical path tube (having a diameter larger than the first tube portion)
15. first optical window
16. first tube portion of second optical path tube (having a diameter smaller than the second tube portion)
17. second tube portion of second optical path tube (having a diameter larger than the first tube portion)
18. second optical window
19. sealing material
20. aperture window
21. third optical path tube
22. gas flow path
23. fluorescence light exit port
24. first tube portion of third optical path tube (having a diameter smaller than the second tube portion)
25. second tube portion of third optical path tube (having a diameter larger than the first tube portion)
26. third optical window
27. cell

The invention claimed is:
1. A cryostat comprising:
a casing in which an inlet port and an exit port are formed;
a cell housing provided in the casing;
temperature control means for adjusting the temperature of the cell;
a first optical path tube for guiding a light beam entering the inlet port of the casing to the cell housing;
a second optical path tube for guiding the light beam that has passed through the cell housing to the exit port of the casing;
a first optical window and a second optical window that are disposed at openings, exposed to the outside, of the first optical path tube and the second optical path tube, respectively; and sealing materials that are disposed at the peripheries of the first and second optical windows to seal the first and second optical path tubes and have a water vapor transmission rate of 30000 cc·cm$^2$·mm·sec·cm Hg×10$^{10}$ or lower.

2. The cryostat according to claim 1, wherein the largest diameters of the first and second optical windows are each 16 mm or larger.

3. The cryostat according to claim 1, wherein the first and second optical path tubes contain an ethylene fluoride resin.

4. The cryostat according to claim 1, wherein the sealing materials contain a fluorine-containing polymer and/or a butyl rubber.

5. The cryostat according to claim 4, wherein the fluorine-containing polymer is at least one member selected from a binary fluororubber and a ternary fluororubber.

6. The cryostat according to claim 1, further comprising an aperture window for restricting a light beam entering the first optical window.

7. The cryostat according to claim 1, further comprising a gas flow path for feeding a gas to the first optical path tube and/or the second optical path tube.

8. A circular dichroism spectrometer comprising the cryostat according to claim 1.

* * * * *